(12) United States Patent
Jain et al.

(10) Patent No.: US 7,244,316 B2
(45) Date of Patent: ***Jul. 17, 2007

(54) METHODS OF MAKING GAS SENSORS AND SENSORS FORMED THEREFROM

(75) Inventors: Kailash Jain, Troy, MI (US); Kenneth Rahmoeller, West Bloomfield, MI (US); Da Yu Wang, Troy, MI (US); Eric Clyde, Bay City, MI (US); Paul Kikuchi, Fenton, MI (US)

(73) Assignee: Delphi Technologies, Inc., Troy, MI (US)

(*) Notice: Subject to any disclaimer, the term of this patent is extended or adjusted under 35 U.S.C. 154(b) by 630 days.

This patent is subject to a terminal disclaimer.

(21) Appl. No.: 10/439,137

(22) Filed: May 15, 2003

(65) Prior Publication Data

US 2004/0226832 A1    Nov. 18, 2004

(51) Int. Cl.
B08B 3/04       (2006.01)
G01N 27/407   (2006.01)
(52) U.S. Cl. .......................... 134/28; 134/29; 204/402; 204/429
(58) Field of Classification Search ............... 204/424, 204/428, 429, 402; 134/28, 29, 26, 27; 73/23.32
See application file for complete search history.

(56) References Cited

U.S. PATENT DOCUMENTS

| | | |
|---|---|---|
| 4,136,000 A | 1/1979 | Davis et al. |
| 5,433,830 A | 7/1995 | Kawai et al. |
| 5,492,612 A | 2/1996 | Kennard, III et al. |
| 6,179,989 B1 | 1/2001 | Kennard, III et al. |
| 6,382,198 B1 | 5/2002 | Smith et al. |
| 6,479,435 B1 | 11/2002 | Pulman et al. |
| 6,479,436 B1 | 11/2002 | Otten et al. |
| 6,514,397 B2 | 2/2003 | LaBarge et al. |
| 6,544,467 B2 | 4/2003 | Symons et al. |
| 6,555,159 B2 | 4/2003 | Clyde et al. |
| 6,562,747 B2 | 5/2003 | Symons et al. |
| 6,585,872 B2 | 7/2003 | Donelon et al. |
| 6,616,820 B2 | 9/2003 | Wang et al. |
| 6,638,405 B2 | 10/2003 | Jain et al. |
| 6,916,384 B2 * | 7/2005 | Jain et al. ..................... 134/28 |
| 2003/0075440 A1 | 4/2003 | Jain et al. |

\* cited by examiner

*Primary Examiner*—Kaj K. Olsen
(74) *Attorney, Agent, or Firm*—Paul Marshall (57) ABSTRACT

A two-step chemical treatment method for chemically conditioning a sensor element comprising an electrolyte in ionic communication with a first electrode and a second electrode is described. The method comprises treating at least a portion of a sensor element with a first solution comprising an inorganic base, a carbonate salt and an acid salt; heating the sensor element; treating at least a portion of the sensor element with a second solution comprising an inorganic base and a carbonate salt; and drying the sensor element. The gas sensors comprising the two-step treated sensor elements have reduced lean shift, green effect, sensor output amplitude drop, and the light-off time is improved.

16 Claims, 5 Drawing Sheets

METHODS OF MAKING GAS SENSORS AND SENSORS FORMED THEREFROM

BACKGROUND

The present disclosure relates to sensors, and more particularly to gas, e.g., oxygen, sensors.

Sensors, in particular gas sensors, have been utilized for many years in several industries (e.g., flues in factories, in furnaces and in other enclosures; in exhaust streams such as flues, exhaust conduits, and the like; and in other areas). For example, the automotive industry has used exhaust gas sensors in automotive vehicles to sense the composition of exhaust gases, namely, oxygen. A sensor may be used to determine the exhaust gas content for alteration and optimization of the air to fuel ratio for combustion.

One type of sensor employs an ionically conductive solid electrolyte between porous electrodes. For oxygen detection, solid electrolyte sensors are used to measure oxygen activity differences between an unknown gas sample and a known gas sample. In the application of a sensor for automotive exhaust, the unknown gas is exhaust and the known gas, i.e., reference gas, is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force (EMF) is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("sensing electrode"), and a porous electrode exposed to the partial pressure of a known gas ("reference electrode"). Sensors used for automotive applications typically employ a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity at low exhaust temperatures. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas Due to the large difference in oxygen partial pressure between fuel rich and fuel lean exhaust conditions, the electromotive force (EMF) changes sharply at the stoichiometric point, giving rise to the characteristic switching behavior of these sensors. Consequently, these potentiometric oxygen sensors indicate qualitatively whether the engine is operating in fuel rich or fuel lean conditions, without quantifying the actual air to fuel ratio of the exhaust mixture.

In addition to oxygen, the exhaust gas contains many components including carbon monoxide, carbon dioxide, hydrogen, water, nitrogen oxides, nitrogen, and a variety of hydrocarbons and hydrocarbon derivatives. Because the exhaust gas is a non-equilibrium mixture containing products of incomplete combustion, the oxygen partial pressure is not an equilibrium pressure. Because the oxygen partial pressure is not at equilibrium, sensors do not operate at stoichiometric air to fuel ratios per the Nernst equation. In addition, the use of zirconia-based electrolyte materials contributes to non-ideal sensor behavior.

To provide a means of monitoring the cell potential and circumvent at least some of the difficulties associated with non-equilibrium conditions, catalytic electrodes are used to both catalyze the oxidation reactions and to equilibrate the local oxygen concentrations. Ideal sensors produce a sharp EMF or voltage step at a stoichiometric air to fuel ratio per the Nernst equation. Manufactured sensors, however, exhibit non-ideal behaviors, for example, a broadened voltage transition that occurs over a range of air to fuel ratios near the stoichiometric ratio. In addition, the sensor EMF may depend upon mass transport processes, adsorption, desorption and chemical reactions that occur at the electrodes. There is some evidence that broadened voltage transitions and non-ideal behavior are due to a loss in catalytic activity of the electrodes. Below about 600° C., the sensor internal electrochemical factors such as electrode polarization and electrode impedance also contribute to non-ideal behavior. Many commercial sensors cease to function at about 400° C.

In order to improve sensor performance characteristics, electrolytic and chemical conditioning techniques have been utilized. Electrolytic conditioning typically involves applying static or pulsed currents to a heated sensor element in a reducing or air environment. Chemical conditioning typically consists of acid treatment (e.g., with HF, HCl, $HNO_3$, etc.) and noble metals or noble metal salts (e.g., Pt, Rh, $H_2PtCl_6$, etc.) followed by heating to accomplish the reactions. Many prior conditioning treatments require up to six treatment steps. While suitable for their intended purpose, such treatments are costly to perform, often require the use of toxic chemicals such as hydrogen fluoride, and are inherently limited by the quality of the electrolyte and electrode films.

There thus remains a need for additional sensors and methods for producing and treating sensors elements that improve the response characteristics of the sensor.

SUMMARY

Disclosed herein are gas sensors, methods of treating gas sensor elements, and methods for making gas sensor elements. In one embodiment, a method of treating a gas sensor element comprises applying a first solution comprising an inorganic base, a carbonate salt and an acid salt to at least a portion of the sensor element; heating the sensor element; applying a second solution comprising an inorganic base and a carbonate salt to the portion of the sensor element; and drying the sensor element; wherein the gas sensor element comprises an electrolyte in ionic communication with a first electrode and a second electrode.

In another embodiment, a method of producing a gas sensor element comprises disposing a reference electrode on a first side of an electrolyte; disposing a sensing electrode on a second side of the electrolyte; sintering the reference electrode, the electrolyte and the sensing electrode to form an untreated gas sensor element; applying a first solution comprising an inorganic base, a carbonate salt and an acid salt to at least a portion of the untreated gas sensor element; heating the sensor element; applying a second solution comprising an inorganic base and a carbonate salt to the portion of the sensor element; and drying the sensor element.

In another embodiment, provided is a gas sensor comprising a sensor element made by the above-describe method.

The above described and other features are exemplified by the following figures and detailed description.

BRIEF DESCRIPTION OF THE DRAWINGS

Referring now to the figures, wherein like elements are numbered alike in several figures.

DETAILED DESCRIPTION

As-manufactured sensor elements are often not suitable for use in engine control sensors due to high internal resistance, low amplitude signal voltage, lean shift, etc. As used herein, a gas sensor element comprises an electrolyte in ionic communication with a first electrode and a second electrode. The first step comprises treating at least a portion of a sensor element with a first solution comprising an inorganic base, a carbonate salt and an acid salt. The second step comprises treatment with a second solution comprising an inorganic base and a carbonate salt to remove the reaction products and excess salts. The two-step process improves the sensor performance because there is little or no change in the electrode microstructure, the oxygen exchange reactions at the electrodes are improved, and the salts retained from the treatment process reduce mixed potential effects thus minimizing the lean shift. The gas sensors comprising the sensor elements treated by the disclosed two-step process exhibit improved response characteristics as compared to prior sensors. Preferably, the sensor is effective at nearly stoichiometric conditions at temperatures as low as about 370° C., in the absence of heating.

Although described in connection with an oxygen sensor, it is to be understood that the two-step conditioning treatment can be employed with any type of sensor, such as nitrogen oxide sensor, hydrogen sensor, hydrocarbon sensor, and the like. Although described in connection with a planar sensor and a conical sensor, it is to be understood that the two-step conditioning treatment can be employed with any type of sensor, such as a wide-range, switch-type, and the like.

Figure 1:
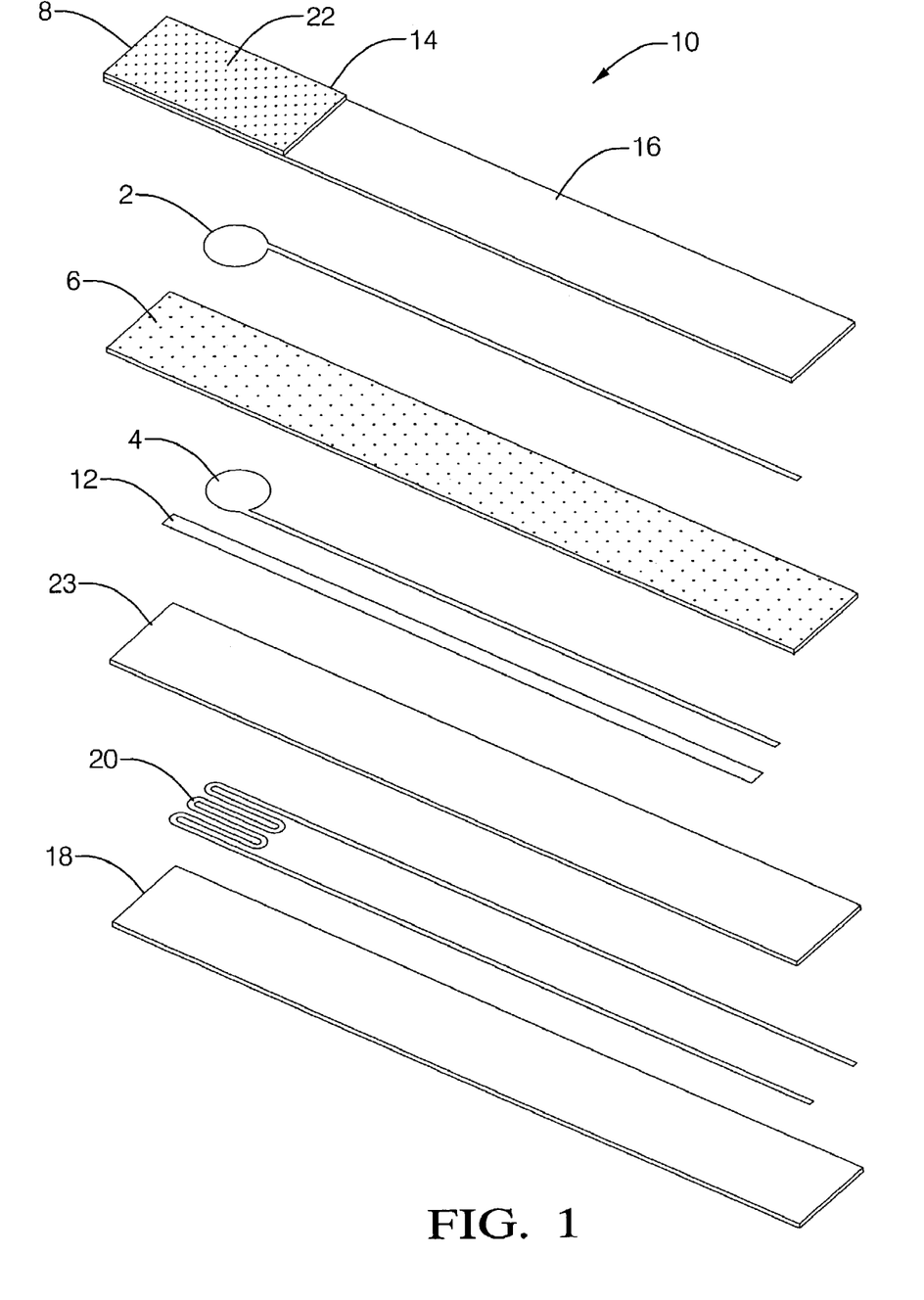
FIG. 1 is an expanded view of one embodiment of a planar oxygen sensor element.

Referring to FIG. 1, an exemplary planar gas sensor element 10 is illustrated. The sensing (i.e., first, exhaust gas or outer) electrode 2 and the reference gas (i.e., second or inner) electrode 4 are disposed on opposite sides of, and adjacent to, an electrolyte layer 6 creating an electrochemical cell (2/6/4). On the side of the sensing electrode 2, opposite solid electrolyte 6, is a protective layer 8 that enables fluid communication between the sensing electrode 2 and the exhaust gas. This protective layer may optionally comprise a porous portion 14 disposed adjacent to the sensing electrode 2 and a solid portion 16. Disposed over at least a portion of the protective layer 8, adjacent to the sensing electrode 2 can be a protective coating 22.

Meanwhile, disposed on the side of the reference electrode 4 opposite solid electrolyte 6, can be an optional reference gas channel 12, which is in fluid communication with the reference electrode 4 and optionally with the ambient atmosphere and/or the exhaust gas. Disposed on a side of the reference gas channel 12 opposite the reference electrode 4, may optionally be a heater 20 for maintaining sensor element 10 at a desired operating temperature. Disposed between the reference gas channel 12 and the heater 20, as well as on a side of the heater opposite the reference gas channel 12, can be one or more insulating layers 24, 18.

In addition to the above sensor components, other sensor components can be employed, including but not limited to, lead gettering layer(s), leads, contact pads, ground plane layers(s), support layer(s), additional electrochemical cell (s), and the like. The leads, which supply current to the heater and electrodes, are often formed on the same layers as the heater and the electrodes to which they are in electrical communication and extend from the heater/electrode to the terminal end of the gas sensor where they are in electrical communication with the corresponding via (not shown) and appropriate contact pads (not shown).

The electrolyte 6, which may be a solid electrolyte, can be formed of a material that is capable of permitting the electrochemical transfer of oxygen ions while inhibiting the passage of exhaust gases. Possible electrolyte materials include zirconium oxide (zirconia), cerium oxide (ceria), calcium oxide, yttrium oxide (yttria), lanthanum oxide, magnesium oxide, and the like, as well as combinations comprising one or more the foregoing electrolyte materials, such as yttria doped zirconia, and the like.

Disposed adjacent to electrolyte 6 are electrodes 2, 4. The sensing electrode 2, which is exposed to the exhaust gas during operation, preferably has a porosity sufficient to permit diffusion to oxygen molecules therethrough. Similarly, the reference electrode 4, which can be exposed to a reference gas such as oxygen, air, or the like, during operation, preferably has a porosity sufficient to permit diffusion to oxygen molecules therethrough. These electrodes 2,4 can comprise a metal capable of ionizing oxygen, including, but not limited to, platinum, palladium, gold, rhodium, iridium and ruthenium; and metal oxides, such as zirconia, yttria, ceria, calcium oxide, aluminum oxide (alumina), and the like; as well as combinations comprising one or more of the foregoing metals and metal oxides. Other additives such as zirconia may be added to impart beneficial properties such as inhibiting sintering of the platinum to maintain porosity.

Electrodes 2, 4 may optionally be applied in the form of a metal ink or paste. The metal ink preferably comprises noble metals including platinum (Pt), rhodium (Rh), palladium (Pd), and alloys thereof, of which platinum is preferred. The metal ink further comprises an electrolyte material. Suitable electrolyte materials include all those materials suitable for electrolyte 6, of which zirconia, partially or fully stabilized with calcium oxide (CaO), yttrium oxide ($Y_2O_3$), ytterbium (III) oxide ($Yb_2O_3$), scandium oxide ($Sc_2O_3$), and the like, as well as compositions comprising one or more of the foregoing electrolyte materials, is preferred. The metal ink optionally comprises a fugitive material. Suitable fugitive materials include graphite, carbon black, starch, nylon, polystyrene, latex, other soluble organics (e.g., sugars and the like) and the like, as well as compositions comprising one or more of the foregoing fugitive materials. The electrolyte and fugitive materials create uniform or nearly uniform pores during sintering to maintain gas permeability and increase catalytically active surface area. The electrolyte and fugitive materials additionally provide catalytic regions at the electrode-sensor electrolyte interface to extend performance of the sensor down to about 400° C. or even lower. Preferably, the noble metal ink comprises platinum particles of about 0.2 to about 0.5 microns in diameter, about 2.5% yttria stabilized zirconia, and organic vehicles such that the weight of platinum in the ink is about 58 percent by weight (wt. %) to about 65 wt. % based on the total weight of the metal ink.

The metal ink is disposed onto the electrolyte body using a suitable application process including thin or thick film deposition techniques. Suitable deposition techniques include spraying, spinning, dip-coating, and screen printing with dip-coating preferred for conical sensors and screen printing preferred for flat plate sensors. The thickness of the metal ink disposed on the electrolyte may be varied depending on the application method and durability requirements. The thickness of the metal ink can be controlled by dipping the electrolyte in the metal ink and then regulating the dwell time in the ink suspension and the rate at which the electrolyte is withdrawn. Electrode durability increases with thickness, but at the cost of decreased sensor sensitivity. Thus, a balance between durability and sensitivity exists, and as such, the desired balance may be achieved by controlling the thickness of the metal ink during deposition.

Preferably, the thickness of the electrode is less than or equal to about 10 micrometers (μm), with less than or equal to about 7 μm especially preferred, and less than or equal to about 5 μm most preferred. Also preferred is an electrode thickness of greater than or equal to about 0.1 μm, with greater than or equal to about 1 μm more preferred, and greater than or equal to about 3 μm most preferred.

Disposed on a side of sensing electrode 2, opposite electrolyte 6, is a protective layer 8. Protective layer 8 may comprise a spinel (e.g., magnesium aluminate), alumina, zirconia, aluminum oxide, carbon black, and organic binders, as well as combinations comprising one or more of the foregoing materials. Preferably, the protective layer comprises a porous ceramic material comprising aluminum oxide, carbon black, and organic binders. The carbon black acts as a fugitive material to allow for effective pore formation in the protective layer.

Protective layer 8 may be disposed using thin or thick film deposition techniques including sputtering, electron beam evaporation, chemical vapor deposition, screen printing, pad printing, ink jet printing, spinning, spraying, including flame spraying and plasma spraying, dip-coating and the like, of which dip-coating is preferred for conical and screen printing for flat plate sensors. The protective layer 8 may have a thickness of up to about 500 μm, with less than or equal to about 400 μm preferred.

Optional heater 20 can be employed to maintain the sensor element at the desired operating temperature. Heater 20 can be a heater capable of maintaining the end of the sensor adjacent to the electrodes at a sufficient temperature to facilitate the various electrochemical reactions therein. Heater 20, which can comprise, for example, platinum, aluminum, palladium, and the like, as well as mixtures, oxides, and alloys comprising one or more of the foregoing metals can be screen printed or otherwise disposed onto a substrate to a thickness of about 5 micrometers to about 50 micrometers.

Optional insulating layers 23, 18 provide structural integrity (e.g., protect various portions of the sensor element from abrasion and/or vibration, and the like, and provide physical strength to the sensor), and physically separate and electrically isolate various components. The insulating layer(s) can each be up to about 200 micrometers thick or so, with a thickness of about 50 micrometers to about 200 micrometers preferred. The insulating layers 23, 18 can comprise a dielectric material such as alumina, and the like.

In a planar sensor, the sensor element components, e.g., electrodes 2, 4, electrolyte 6, insulating layer(s) 23, 18, heater 20, protective layers 8 and the like, are formed using techniques such as tape casting methods, sputtering, punching and placing, spraying (e.g., electrostatically spraying, slurry spraying, plasma spraying, and the like), dipping, painting, and the like, as well as combinations comprising one or more of the foregoing techniques. Preferably, the electrodes, leads and other layers are formed on green electrolyte sheets (e.g., zirconia, optionally partially or fully stabilized with CaO, $Y_2O_3$, $Yb_2O_3$, $Sc_2O_3$, and the like) or alumina ceramic layers by such methods as screen printing, slurry coating, spraying, transfer printing, or other processes. The electrodes are applied, for example, as electrode inks comprising noble metals and an electrolyte such as yttria stabilized zirconia. The component layers are then stacked and aligned in accordance with the particular type of sensor. The sensor element can be heated to a temperature of about 1475° C. to about 1550° C. for a time sufficient to sinter the layers, with a temperature of about 1490° C. to about 1510° C. and a time of up to about 3 hours preferred, more preferably about 100 to about 140 minutes. Although the layers may be separately calcined, they are preferably co-fired. Optionally, the aligned layers can be heat treated to formed laminated stacks often referred to as "tiles" that contain multiple sensor elements.

Figure 2:
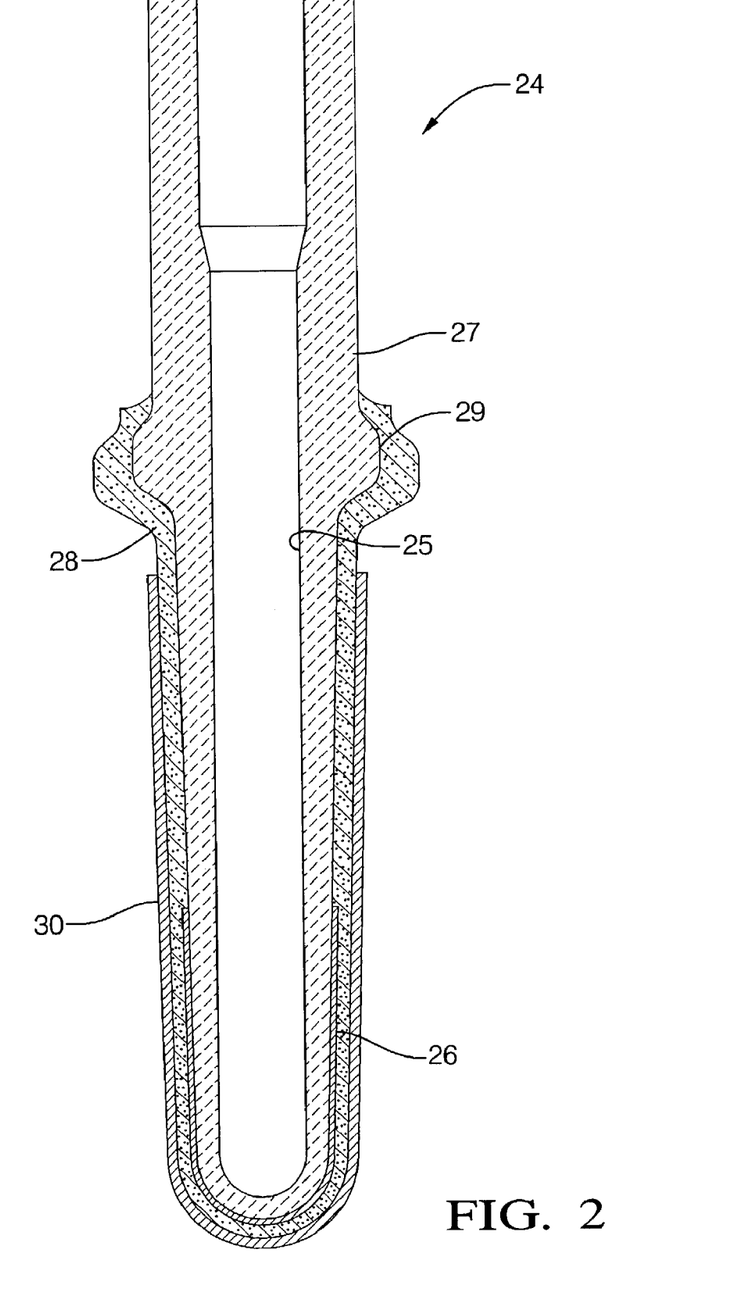
FIG. 2 is a cross-sectional schematic of one embodiment of a conical oxygen sensor.

An alternative sensor design can include a conical sensor 24 as is illustrated in FIG. 2. Conical sensor 24 typically comprises a conically shaped electrolyte 27 with an inner electrode 25 disposed on the inner surface of the electrolyte 27 and an outer electrode 26 disposed on outer surface of the electrolyte 27. An optional protective layer 28, which is disposed over the outer electrode 26, optionally extends over hips 29. Disposed over the sensing electrode 26, and over optional protective layer 28 is protective coating 30. The sensor component materials, as indicated above for the planar sensor, can also be utilized with the conical sensor 24.

After sintering, the as-manufactured sensor element (10 or 24) is chemically conditioned in a two-step process. The first treatment comprises contacting at least a portion of the sensor element with a first solution comprising an inorganic base, a carbonate salt and an acid salt. Suitable inorganic bases include, for example, hydroxides of such metals as lithium, sodium, potassium, rubidium, cesium, potassium, barium, calcium, magnesium, strontium, scandium, trivalent metals such as yttrium and lanthanum, and mixtures comprising one or more of the foregoing inorganic bases. Preferred inorganic bases include, for example, sodium hydroxide, potassium hydroxide, lithium hydroxide, cesium hydroxide, rubidium hydroxide and mixtures thereof. Suitable carbonate salts include, for example, carbonates of such metals as lithium, sodium, potassium, rubidium, cesium, potassium, barium, calcium, magnesium, strontium, scandium, trivalent metals such as yttrium and lanthanum, and mixtures comprising one or more of the foregoing carbonates. Preferred carbonate salts include, for example, sodium carbonate, potassium carbonate, and mixtures thereof. Suitable acid salts include, for example, ionic fluoride salts (e.g., lithium fluoride, sodium fluoride, potassium fluoride, and the like); covalent fluoride salts (e.g., magnesium fluoride, calcium fluoride, barium fluoride, and the like); fluorinating agents (bromine fluoride, silver fluoride, antimony fluoride, and the like); a simple fluoride obtained by dissolving an oxide or a carbonate of, for example, lithium, sodium, potassium, rubidium, potassium, barium, calcium, magnesium, and strontium; an insoluble fluoride in the form of a suspension (e.g., lanthanum fluoride, cesium fluoride, yttrium fluoride, scandium fluoride, and the like); and combinations comprising one or more of the foregoing acid salts. Preferred acid salts include, for example, sodium fluoride, potassium fluoride, and mixtures thereof. A preferred solvent for the solution is water.

While the amounts of the inorganic base, carbonate salt and acid salt can vary over a wide range, preferably about 1 to about 20 wt. % of each based on the total weight of the solution is employed. Within this range, about 5 wt. % to about 10 wt. % of each component is preferred, with about 6 wt. % to about 8 wt. % more preferred. The amounts of the three components may be the same or different.

The first solution is applied to at least a portion of the sintered sensor element by such methods as dipping, painting, spraying, and the like. Preferably, at least the sensing and reference electrodes are treated. The sensor element may then be dried. Drying can be accomplished in air at temperatures of about 20° C. to about 200° C. for a time of about 5 to about 30 minutes. The sensor may then be heated at a temperature of about 200° C. to about 800° C. for a time of about 30 minutes to several hours, with 600° C. and 1 hour preferred.

In the second treatment step, the portion of the sensor element is treated with a second solution comprising a basic solution. The basic solution can comprise, for example, a mixture of an inorganic base and a carbonate salt such as those described for the first solution. Water is the preferred solvent. In the second solution, the inorganic base and the carbonate salt may be each employed at a concentration of about 1 wt. % to about 20 wt. % based on the total weight of the solution. Within this range, a concentration of about 5 wt. % to about 10 wt. % of the inorganic base and about 2 wt. % to about 7 wt. % of the carbonate salt based on the total weight of the solution is preferred.

The second solution is applied to at least a portion of the sensor element by such methods as dipping, painting, spraying, and the like. Preferably, at least the sensing and reference electrodes are treated. The temperature of the second solution may be about 70° C. to about 100° C., preferably about 95° C. to the boiling point of the solution. The time of treatment depends on the concentration of the components in the second solution as well as the temperature of the treatment. A suitable treatment, for example, is treatment in a boiling solution for about one hour. Following the treatment with the second solution, the sensor element is washed in distilled water and dried. The sensor may then be used in engine tests.

Figure 3:
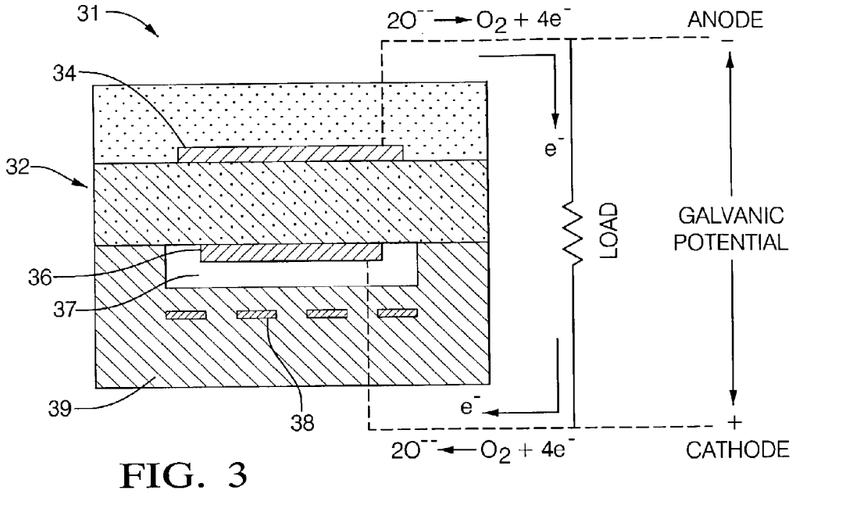
FIG. 3 is a schematic of a galvanic cell using zirconia as an oxygen ion electrolyte.

Referring to FIG. 3, the effects of the above-described process can be described. FIG. 3 shows a schematic of a galvanic cell 31 using zirconia as an oxygen ion electrolyte 32 as is typically found in sensor elements such as those described with reference to FIGS. 1 and 2. In addition to an anode 34 and a cathode 36, the cell can comprise an air channel 37, an alumina layer 38 and a heater 39. A thin membrane of partially stabilized zirconia 32 separates the two gas atmospheres having oxygen partial pressures $P_{O_2}^{ref}$ and $P_{O_2}^{exhaust}$. Each surface of the zirconia membrane has a co-fired noble metal containing electrode that promotes the chemical reactions:

$O_2 + 4e^- \rightarrow 2O^{-2}$ Reference electrode (Cathode 36)
$2O^{-2} \rightarrow O_2 + 4e^-$ Exhaust electrode (Anode 34)

At temperatures below about 600° C., performance of the sensor element often deteriorates (e.g., reduced voltage amplitude, lean shift, low and asymmetric response times, etc.). These performance problems are due, at least in part, to low electrolyte conductivity, high electrode impedance, and low catalytic activity of the anode and cathode electrodes 34, 36 possibly due to a silica rich glassy layer. The glassy layer, at least in part, results from the added materials (e.g., Si, Na, carbon black, etc.) that promote sintering, minimize the mismatch between the thermal expansion coefficients of the layers, and yield increased mechanical strength. Such glassy layers may interfere with oxygen exchange reactions occurring at the electrodes and may contribute to the non-ideal behavior of the sensor.

It is believed that more ideal sensor behavior can be achieved by devitrifying and leaching the glassy layer covering the sensor element using the disclosed two-step treatment process. The salts in the first and second solution devitrify the glassy layer to form an aqueous soluble composition. In addition, the small amounts of salt residue that remain after treatment can modify the adsorption characteristics of the surface reducing the mixed potential effects and minimizing the lean shift observed for the sensor.

The residue of the first solution and the second solution may be found on both the electrodes and the protective layers. The residue preferably comprises a mixture of carbonate salts, fluoride salts and/or oxides resulting from decomposition of carbonates in an amount of about 0.025 to about 0.5 grams per cubic inch ($g/in^3$) of sensor element volume. Within this range, an amount of carbonate salt, fluoride salt and oxide mixture of less than or equal to about 0.4 $g/in^3$ is preferred, with less than or equal to about 0.3 $g/in^3$ more preferred. Also preferred within this range is an amount of carbonate and fluoride salt mixture of greater than or equal to about 0.1 $g/in^3$, with greater than or equal to about 0.2 $g/in^3$ more preferred.

EXAMPLES

Methods:

Method of sensor treatment: A planar sensor element having an electrolyte comprising zirconia and electrodes comprising platinum was formed and sintered. The sintered sensor element was then treated as follows. A first solution comprising 3.5 wt. % sodium hydroxide, 3.5 wt. % potassium hydroxide, 7.0 wt. % potassium carbonate and 7.0 wt. % potassium fluoride in water was formed. Approximately 20 milligrams of the first solution was applied to each of the electrodes, dried, and the sensor element was heated to 600°

C. for 1 hour, or to 700° C. for 45 minutes. A second solution was formed comprising 7 wt. % sodium hydroxide and 3 wt. % sodium carbonate. The sensor element was treated in the boiling second solution for about 1 hour. The sensor element was rinsed in deionized water, dried, and packaged for use in engine tests.

Figure 4:
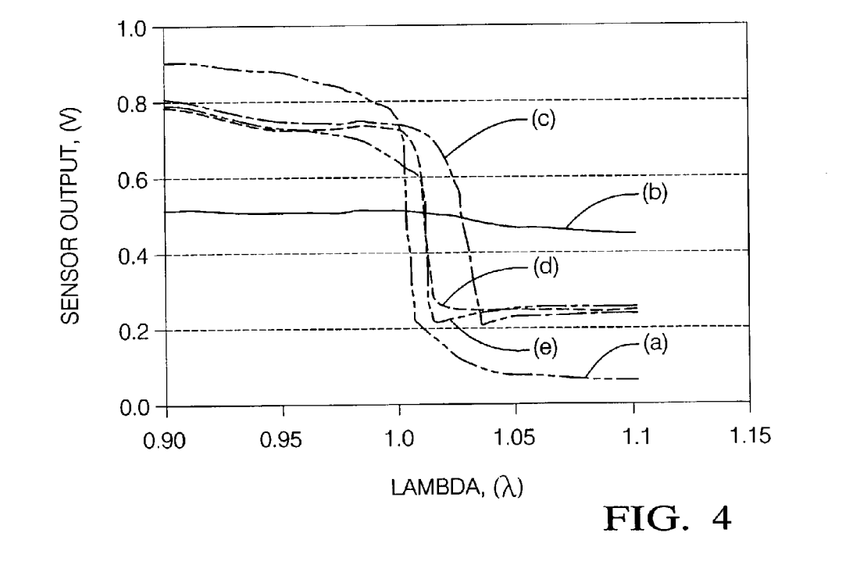
FIG. 4 is a comparison of the switching characteristic of several prior art sensors.

Sensor performance tests were conducted on a 3.8 L V6 engine. The 3.8 L V6 engine was run in open loop mode with perturbation of ±2.5% (±0.3 A/F (air to fuel ratio)). Comparative Example 1: Experiments were conducted to show the effectiveness of the proposed two-part method compared to prior art methods which required up to six chemical treatment steps. FIG. 4 shows the results for several prior art sensors. Curve (a) is for a conical sensor having a heater. Curves (b) to (e) are for flat-plate sensors which do not employ heaters. Curve (b) is for a flat plate sensor treated by electrical aging followed by hydrofluoric acid treatment (EHF) treatment according to U.S. Pat. No. 6,179,989; curve (c) is for a six-step treated sensor treated with sodium hydroxide and hydrochloric acid and also sodium and potassium enhanced; curve (d) is for a six-step treated sensor treated with sodium hydroxide and hydrochloric acid, promoted with platinum and ruthenium, and also sodium and potassium enhanced; and curve (e) is for a six-step treated sensor treated with sodium hydroxide and hydrochloric acid, treated with potassium fluoride at 950° C. in a nitrogen atmosphere, and sodium and potassium enhanced. The three sensors produced by the six-step processes (curves (c), (d) and (e)), are significantly better than that for the sensor produced by the EHF method (curve (b)), e.g., curves (c), (d) and (e) show better sensor output voltages and are less lean-shifted than curve (b). While the performance exhibited by the six-step processed sensors is superior to the EHF processed sensor, the S-curves for the six-step processed sensors are significantly lean-shifted as compared to the heated reference conical sensor shown in curve (a).

Example 1

Figure 5:
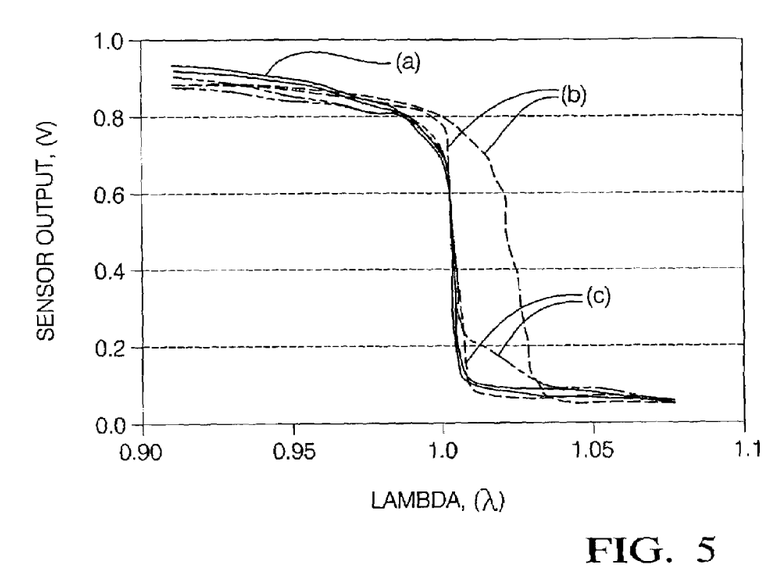
FIG. 5 shows the switching characteristics of the disclosed two-step treated sensor at 450° C. compared to a prior art flat plate sensor.

FIG. 5 shows the performance of a two-step treated sensor according to the present disclosure (curve (a)) compared to an EHF-treated heated sensor (curve (b)) and a heated conical reference sensor (curve (c)) on a 3.8 L V6 engine at 450° C. exhaust gas temperature. The two-step treated sensor of the present disclosure (curve (a)) exhibits less lean shifted behavior than the than the six-step treated sensor shown in FIG. 4 (curves c, d, and e) (lambda=1 represents a stoichiometric air to fuel ratio, lambda>1 represents leaner air to fuel ratios). In addition, the two-step treated sensor of the present disclosure was 0.25 less shifted with respect to hysteresis between lean and rich transitions as compared to the EHF-treated sensor (compare curve (a) to curve (b)). Further, the unheated two-step treated sensor of the present disclosure performed comparably to the heated conical sensor (compare curve (a) to curve (c)).

Example 2

Figure 6:
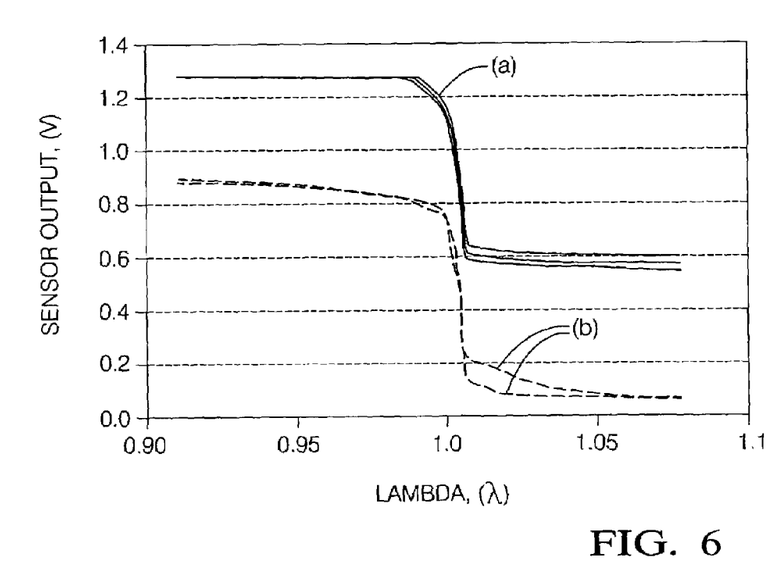
FIG. 6 shows the switching characteristics of the disclosed two-step treated sensor at 370° C. compared to a prior art flat plate sensor.

FIG. 6 shows the performance of a two-step treated sensor according to the present disclosure (curve (a)) compared to a heated conical reference sensor (curve (b)) on a 3.8 L V6 engine at 370° C. During the experiment, 5 microamperes of oxygen was pumped into the flat-plate sensor reference electrode to maintain the integrity of the air reference electrode. First, the S-curves show that the two-step treatment of the present disclosure provides sensors having reproducible performance. Second, the sensor voltage amplitude ($V_{max}-V_{min}$) for the two-step treated sensor is about 0.6 volts higher and 0.035 less lean shifted from the stoichiometric air to fuel ratio than a comparable EHF treated sensor (see FIG. 4, curve (b)). Third, the rich to lean transition is even slightly better than the heated conical reference sensor. Fourth, both the rich to lean and the lean to rich transition are symmetrical and show little hysteresis.

Example 3

Figure 7:
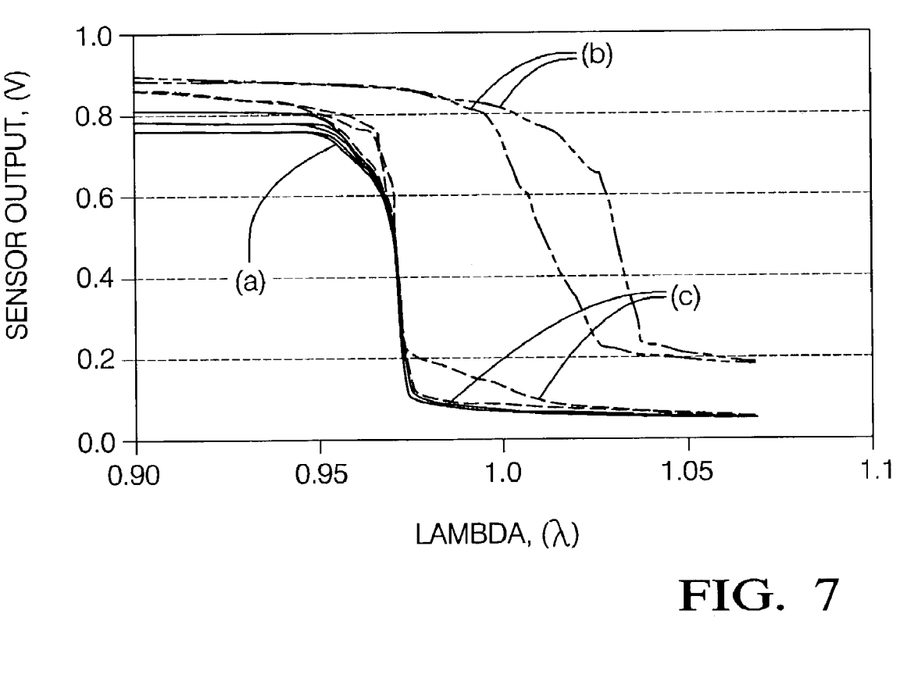
FIG. 7 shows the switching characteristics of the disclosed two-step treated sensor at 370° C. compared to a prior art conical sensor.

As shown in FIG. 7, the performance of a sensor produced by the disclosed two-step process (curve (a)) is also improved compared to a conventional planar sensor (curve (b)) when both sensors are operated in unheated mode on a 3.8 L V6 engine at 370° C. Curve (c) is a reference heated comical sensor. In this experiment, for the flat-plate sensors, the internal resistance drop due to the pump current was subtracted. Also, the output of the planar sensors matches the reference sensor in the rich region, but in the graph the output appears to level off due to limitation of output voltage in the measurement system. While the sensor voltage amplitude of the sensor produced by the two-step method is comparable to that of the conventional planar sensor, the two-step treated sensor is about 0.035 less lean shifted from the stoichiometric air to fuel ratio and about 0.025 less hysteretic during rich to lean and lean to rich transitions. In data not shown, the effect of 100 hours of aging on the engine on the sensor prepared by the two-step method was minimal, resulting in less than a 0.002 shift in the air to fuel ratio in steady-state switching conditions.

Without being held to theory, it is believed that the disclosed two-step treatment process devitrifies a thin (about 50 nanometer) silica rich glassy layer covering the electrode and/or the electrolyte surfaces. The detailed composition of the glassy layer depends upon the composition of the protective layers and the raw materials used in sensor element fabrication. Devitrification of the glassy layer covering the porous protection coating is accomplished by treating with the first solution comprising an inorganic base, a carbonate salt and an acid salt. The devitrification increases electrocatlytic activity and oxygen adsorption. In addition, treating with the second solution comprising an inorganic base and a carbonate salt reduces the interference of the glassy layer to diffusing species. The small amounts of the salts retained in the sensor element from the two treatment steps also help to improve the mobility of oxygen over the electrode and at triple point catalytic regions leading to efficient adsorption of oxygen atoms. This combined effect is expected to make the electrode electrocatalytic. This conclusion is supported by several lines of evidence. First, the absence of hysteresis in lean and rich transitions in the steady state switching characteristics in the two-step treated sensors operated on a V6 engine at 370° C. and 440° C. The sensors produced by the disclosed methods preferably have a hysteresis between the rich to lean and lean to rich states of less than about 0.0015 lambda, preferably less than about 0.001 lambda, at 370° C. Second, the unheated two-step treated sensors have switching characteristics that are closer to lambda equal to 1 on a V6 engine operating at a 370° C. operating temperature than a heated reference or an unheated commercial sensor. The sensors produced by the disclosed methods are preferably shifted less than about 0.007 lambda from the stoichiometric air to fuel ratio, more preferably less than about 0.006, at a temperature of 370° C. Third, the low temperature performance (i.e., at 370° C.) and engine aging data imply that the green effect (i.e., the effect of engine aging) is reduced and the light-off times are fast. Preferably, the sensor after 100 hours of aging on the engine, is less than about 0.009 shifted in air to fuel ratio, preferably less than 0.007 at a temperature of 370° C., compared to the air to fuel ratio prior to testing.

In the two-step treatment process, the carbonates are believed to reduce the hysteresis between the rich and lean transitions and enhance the sensor amplitude to be closer to that predicted by the Nernst equation. In addition, the carbonates and fluorides are expected to collectively change the adsorption properties of the electrode surface leading to switching close to stoichiometric air to fuel ratio. The effects together produce reduced sensitivity in the sensor to trace levels of unreacted gas in the exhaust. The lean shift, green effect, sensor output amplitude drop and its temperature-dependence are all reduced, and the light-off time is improved.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for treating a gas sensor element, the method comprising:
    applying a first solution comprising an inorganic base, a carbonate salt and an fluoride salt to at least a portion of the sensor element;
    heating the sensor element;
    applying a second solution comprising an inorganic base and a carbonate salt to the portion of the sensor element; and
    drying the sensor element;
    wherein the gas sensor element comprises an electrolyte in ionic communication with a first electrode and a second electrode.

2. The method of claim 1, wherein the first solution comprises about 1 weight percent to about 20 weight percent independently of each of the inorganic base, the carbonate salt and the fluoride salt, based upon the total weight of the first solution.

3. The method of claim 1, wherein the second solution comprises about 1 weight percent to about 20 weight percent independently of each of the inorganic base and the carbonate salt, based upon the total weight of the second solution.

4. The method of claim 1, wherein the inorganic base and the carbonate salt of the first solution each independently comprises lithium, sodium, potassium, rubidium, cesium, potassium, barium, calcium, magnesium, strontium, scandium, yttrium, lanthanum, or a mixture of one or more of the foregoing metals.

5. The method of claim 4, wherein the inorganic base is sodium hydroxide, potassium hydroxide, or a mixture comprising one or more of the foregoing hydroxides.

6. The method of claim 4, wherein the carbonate salt is sodium carbonate, potassium carbonate, or a mixture comprising one or more of the foregoing carbonate salts.

7. The method of claim 1, wherein the fluoride salt of the first solution is selected from the group consisting of lithium fluoride; sodium fluoride; potassium fluoride; magnesium fluoride; calcium fluoride; barium fluoride; bromine fluoride; silver fluoride; antimony fluoride; lanthanum fluoride; cesium fluoride; yttrium fluoride; scandium fluoride; or a mixture of one or more of the foregoing fluoride salts.

8. The method of claim 7, wherein the fluoride salt is sodium fluoride, potassium fluoride, or a mixture comprising one or more of the foregoing fluoride salts.

9. The method of claim 1, wherein the inorganic base and the carbonate salt of the second solution each independently comprises lithium, sodium, potassium, rubidium, cesium, potassium, barium, calcium, magnesium, strontium, scandium, yttrium, lanthanum, or a mixture of one or more of the foregoing metals.

10. A method of producing a gas sensor element, comprising:
    disposing a reference electrode on a first side of an electrolyte;
    disposing a sensing electrode on a second side of the electrolyte;
    sintering the reference electrode, the electrolyte and the sensing electrode to form an untreated gas sensor element;
    applying a first solution comprising an inorganic base, a carbonate salt and a fluoride salt to at least a portion of the untreated gas sensor element;
    heating the sensor element;
    applying a second solution comprising an inorganic base and a carbonate salt to the portion of the sensor element; and
    drying the sensor element.

11. The method of claim 10, wherein the first solution comprises about 1 weight percent to about 20 weight percent independently of each of the inorganic base, the carbonate salt and the fluoride salt, based upon the total weight of the first solution, and wherein the inorganic base and the carbonate salt of the first solution each independently comprise a metal selected from the group consisting of lithium, sodium, potassium, rubidium, cesium, potassium, barium, calcium, magnesium, strontium, scandium, yttrium, lanthanum, or a mixture of one or more of the foregoing metals.

12. The method of claim 10, wherein the second solution comprises about 1 weight percent to about 20 weight percent independently of each of the inorganic base and the carbonate salt, based upon the total weight of the second solution, and wherein the inorganic base and the carbonate salt of the second solution each independently comprises lithium, sodium, potassium, rubidium, cesium, potassium, barium, calcium, magnesium, strontium, scandium, yttrium, lanthanum, or a mixture of one or more of the foregoing metals.

13. The method of claim 10, wherein the electrolyte comprises zirconia.

14. The method of claim 10, wherein the sensing electrode comprises a noble metal.

15. The method of claim 10, wherein the sensor element further comprises about 0.05 to about 0.3 grams per cubic inch of the residue of the first solution and the second solution.

16. The method of claim 10, wherein the sensor element further comprises a protective layer and wherein the protective layer comprises about 0.1 to about 0.2 grams per cubic inch of the residue of the first solution and the second solution.

* * * * *